(12) United States Patent
Gong et al.

(10) Patent No.: US 9,740,967 B2
(45) Date of Patent: Aug. 22, 2017

(54) METHOD AND APPARATUS OF DETERMINING AIR QUALITY

(71) Applicant: International Business Machines Corporation, Armonk, NY (US)

(72) Inventors: Min Gong, Shanghai (CN); Yu Wang, Beijing (CN); Zhi H. Wang, Beijing (CN); Junchi Yan, Shanghai (CN); Chao Zhang, Beijing (CN); Qian K. Zhao, Shanghai (CN); Jun Zhu, Beijing (CN)

(73) Assignee: International Business Machines Corporation, Armonk, NY (US)

( * ) Notice: Subject to any disclaimer, the term of this patent is extended or adjusted under 35 U.S.C. 154(b) by 0 days.

(21) Appl. No.: 15/018,005

(22) Filed: Feb. 8, 2016

(65) Prior Publication Data

US 2016/0155027 A1    Jun. 2, 2016

Related U.S. Application Data

(63) Continuation of application No. 14/527,132, filed on Oct. 29, 2014, now Pat. No. 9,317,732.

(30) Foreign Application Priority Data

Oct. 31, 2013   (CN) .......................... 2013 1 0530879

(51) Int. Cl.
*G06K 9/62* (2006.01)
*G06K 9/66* (2006.01)
(Continued)

(52) U.S. Cl.
CPC .................. *G06K 9/66* (2013.01); *G01J 1/42* (2013.01); *G01N 33/0062* (2013.01); *G06K 9/00* (2013.01); *G06K 9/6256* (2013.01)

(58) Field of Classification Search
CPC ............... G06Q 30/0252; G01N 21/00; G01N 21/3504; G01N 33/0004
(Continued)

(56) References Cited

U.S. PATENT DOCUMENTS

| 6,526,268 B1 * | 2/2003 | Marrah | G08G 1/093 455/186.1 |
| 7,013,203 B2 * | 3/2006 | Moore | F03D 7/047 290/44 |

(Continued)

FOREIGN PATENT DOCUMENTS

| CA | 2834217 A1 | 11/2012 |
| CN | 102162788 A | 8/2011 |

(Continued)

OTHER PUBLICATIONS

Mishra (http://www.ipublishing.co.in/jggsvol1no12010/voltwo/EIJGGS3062.pdf).*

(Continued)

*Primary Examiner* — Yosef Kassa
(74) *Attorney, Agent, or Firm* — Maeve Carpenter

(57) ABSTRACT

In an approach to determining an air quality based on image, a computer performs a method, the method comprising: determining an image to be measured; determining an air quality model of at least one key area, the at least one key area including a key area associated with the image to be measured; acquiring a reference clear image corresponding to the image to be measured; and determining an air quality index to be measured based on an air quality related feature extracted from the image to be measured, the corresponding reference clear image, and the determined air quality model of the key area associated with the image to be measured.

20 Claims, 4 Drawing Sheets

(51) Int. Cl.
G06K 9/00 (2006.01)
G01J 1/42 (2006.01)
G01N 33/00 (2006.01)

(58) Field of Classification Search
USPC ....... 382/159, 170, 172, 190, 209, 278, 307, 382/103, 109, 206; 356/433, 437, 438, 356/456
See application file for complete search history.

(56) References Cited

U.S. PATENT DOCUMENTS

| | | | |
|---|---|---|---|
| 7,016,045 B2 | 3/2006 | Kwon | |
| 7,103,370 B1 * | 9/2006 | Creemer | G06Q 30/02 455/456.1 |
| 7,272,251 B2 | 9/2007 | Acar | |
| 7,286,925 B2 * | 10/2007 | Lang | G01F 1/72 701/114 |
| 7,378,954 B2 * | 5/2008 | Wendt | G01D 9/005 250/370.07 |
| 7,616,305 B2 * | 11/2009 | Murnick | G01N 21/1717 356/311 |
| 7,787,003 B2 | 8/2010 | Sowa | |
| 7,899,207 B2 | 3/2011 | Mian et al. | |
| 8,038,944 B1 | 10/2011 | Gordon | |
| 8,140,076 B2 * | 3/2012 | Ponce de Leon | H04W 36/30 370/328 |
| 8,144,180 B2 | 3/2012 | Uduki | |
| 8,159,661 B2 | 4/2012 | S. Moshe | |
| 8,204,786 B2 * | 6/2012 | LeBoeuf | A61B 5/0205 128/920 |
| 8,241,219 B2 | 8/2012 | Anderson | |
| 8,291,752 B2 * | 10/2012 | Bierl | F02B 39/16 73/114.77 |
| 8,442,424 B2 * | 5/2013 | Socolof | G06Q 10/02 455/2.01 |
| 8,583,597 B2 * | 11/2013 | Atamna | G06F 17/3038 707/634 |
| 8,595,020 B2 * | 11/2013 | Marino | G01N 21/3504 23/314 |
| 8,610,066 B2 * | 12/2013 | Wallin | G01N 21/276 250/338.1 |
| 2011/0110558 A1 | 5/2011 | Branham et al. | |

FOREIGN PATENT DOCUMENTS

| | | |
|---|---|---|
| CN | 102254330 A | 11/2011 |
| CN | 103218622 A | 7/2013 |
| CN | 201310530879.6 A | 10/2013 |
| EP | 0632268 A1 | 1/1995 |
| WO | 2011002272 A1 | 1/2011 |

OTHER PUBLICATIONS

Amritphale, "A Digital Image Processing Method for Detecting Pollution in the Atmosphere from Camera Video", UNLV University Libraries, May 1, 2013, <http://digitalscholarship.unlv.edu/cgi/viewcontent.cgi?article=2794&context=thesesdissertations>.
Babari et al., "Visibility Monitoring using Conventional Roadside Cameras—Emerging Applications", Dec. 30, 2011, <http://hautiere.nicolas.free.fr/pdf/2012/hautiere-trc12.pdf>.
Coben, "PM2.5 Sampling Instrument Introduction", Jan. 2, 2012, <http://blog.163.com/lwg8829@126/blog/static/115989453201201753412142/>.
Janeiro et al., "Automated Atmospheric Visibility Measurements using a Digital Camera and Image Registration", 2007, <http://home.mit.bme.hu/~kollar/IMEKO-procfiles-for-web/tc4/TC4-15th-lasi-2007/Final_Papers/F091.pdf>.
Poduri et al., "Visibility Monitoring using Mobile Phones", 2010, <http://robotics.usc.edu/~mobilesensing/visibility/MobileAirQualitySensing.pdf>.
Yin et al., "Learning Based Visibility Measuring with Images", ICONP 2011, Part III, LNCS 7064, pp. 711-718, <http://link.springer.com/chapter/10.1007%2F978-3-642-24965-5_80>.
"Approach and System for Air Pollution Monitoring based on Mobile Social Collaboration", IPCOM000192831D, Feb. 4, 2010, <http://ip.com/IPCOM/000192831>.
"The new phone that can detect air quality", Oct. 15, 2014, <http://www.soft6.cominews/201112/01/205873.html>.
U.S. Appl. No. 14/527,132, filed Oct. 29, 2014.
List of IBM Patents or Patent Applications Treated as Related (Appendix P), filed herewith.
Chinese Office Action dated Nov. 17, 2017 from corresponding Chinese Application No. 201310530879.6.

* cited by examiner

METHOD AND APPARATUS OF DETERMINING AIR QUALITY

TECHNICAL FIELD

The invention relates to air quality measurement, more particularly, to a method and apparatus of determining air quality based on image.

BACKGROUND

Outdoor air pollution is the most important one in environmental hazards threatening human life. Currently, fog and haze and other environmental pollutions are becoming more and more serious, which bring severe harm to human health and environment.

A main factor affecting air quality is fine particle, for example, PM2.5 value commonly concerned by people refers to particle whose aerodynamics equivalent diameter is less than or equal to 2.5 microns in environment air, which is also called a fine particle. In addition, PM10 value refers to particle whose aerodynamics equivalent diameter is less than 10 microns. The higher the value, the more serious the air pollution.

Currently, air quality is measured in real time mainly through sensors disposed at various locations, and it should be noted that, although special-purpose sensor is precise in measurement, price of which is expensive, and such sensor can not be disposed at every location due to cost concern. However, distribution of air quality is not uniform and will vary with time. Thus, in order to cope with poor air quality in time, user needs to know air quality at his/her position at any time and anywhere, so as to decide whether to conduct outdoor activity or take necessary protective measure.

In view of above, there is a need to improve current air quality measurement solution and provide a convenient and efficient air quality measurement solution.

SUMMARY

According to a first aspect of the invention, there is provided a method of determining an air quality, the method comprising: determining an image to be measured; determining an air quality model of at least one key area, the at least one key area including a key area associated with the image to be measured; acquiring a reference clear image corresponding to the image to be measured; and determining an air quality index to be measured based on an air quality related feature extracted from the image to be measured, the corresponding reference clear image, and the determined air quality model of the key area associated with the image to be measured.

With a method, a computer system, and a computer program product of the invention, an air quality can be determined based on an image.

BRIEF DESCRIPTION OF THE DRAWINGS

Through the more detailed description of some embodiments of the present disclosure in the accompanying drawings, the above and other objects, features and advantages of the present disclosure will become more apparent, wherein the same reference generally refers to the same components in the embodiments of the present disclosure.

DETAILED DESCRIPTION

Figure 1:
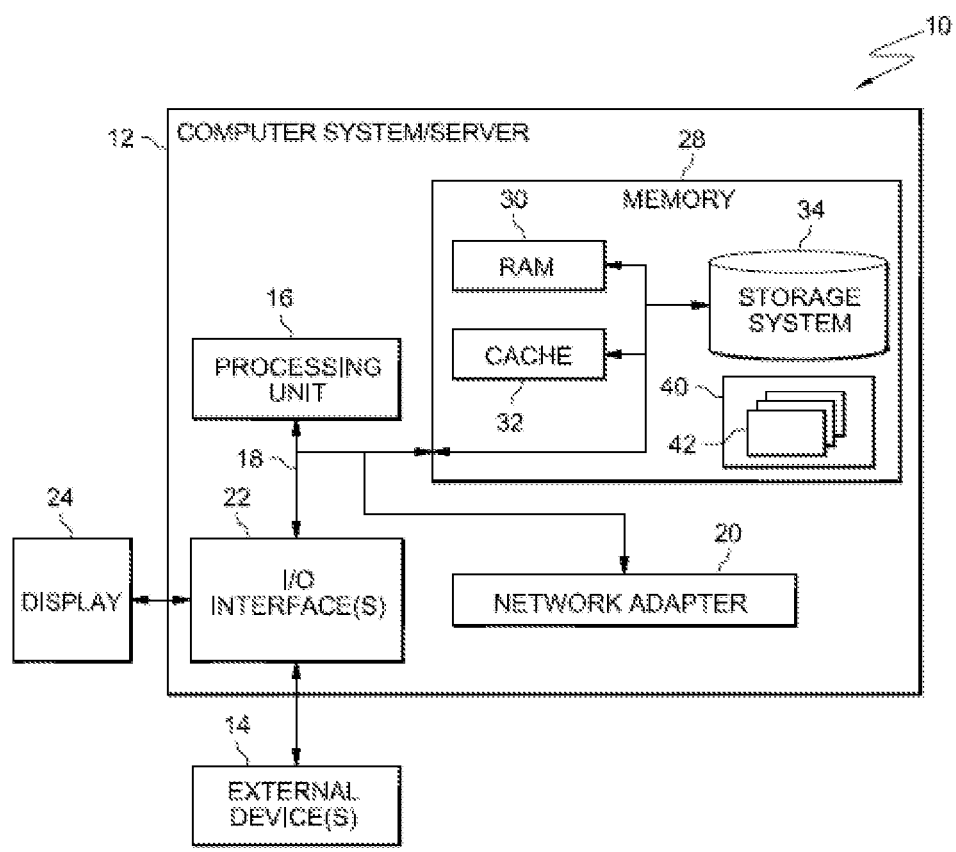
FIG. 1 depicts a block diagram of an exemplary computer system/server which is applicable to implement the embodiments of the invention.

Some preferable embodiments will be described in more detail with reference to the accompanying drawings, in which the preferable embodiments of the present disclosure have been illustrated. However, the present disclosure can be implemented in various manners, and thus should not be construed to be limited to the embodiments disclosed herein. On the contrary, those embodiments are provided for the thorough and complete understanding of the present disclosure, and completely conveying the scope of the present disclosure to those skilled in the art.

As will be appreciated by one skilled in the art, aspects of the present invention may be embodied as a system, method or computer program product. Accordingly, aspects of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, aspects of the present invention may take the form of a computer program product embodied in one or more computer readable medium(s) having computer readable program code embodied thereon.

Any combination of one or more computer readable medium(s) may be utilized. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electromagnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium may be transmitted using any appropriate medium, including but not limited to wireless, wireline, optical fiber cable, RF, etc., or any suitable combination of the foregoing.

Computer program code for carrying out operations for aspects of the present invention may be written in any combination of one or more programming languages, including an object oriented programming language such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of the present invention are described below with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

Referring now to FIG. 1, in which a block diagram of an exemplary computer system/server 12 which is applicable to implement the embodiments of the present invention is shown. Computer system/server 12 is only illustrative and is not intended to suggest any limitation as to the scope of use or functionality of embodiments of the invention described herein.

As shown in FIG. 1, computer system/server 12 is shown in the form of a general-purpose computing device. The components of computer system/server 12 may include, but are not limited to, one or more processors or processing unit(s) 16, a system memory 28, and a bus 18 that couples various system components including system memory 28 to processor 16.

Bus 18 represents one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnect (PCI) bus.

Computer system/server 12 typically includes a variety of computer system readable media. Such media may be any available media that is accessible by computer system/server 12, and it includes both volatile and non-volatile media, removable and non-removable media.

System memory 28 can include computer system readable media in the form of volatile memory, such as random access memory (RAM) 30 and/or cache memory 32. Computer system/server 12 may further include other removable/non-removable, volatile/non-volatile computer system storage media. By way of example only, storage system 34 can be provided for reading from and writing to a non-removable, non-volatile magnetic media (not shown and typically called a "hard drive"). Although not shown, a magnetic disk drive for reading from and writing to a removable, non-volatile magnetic disk (e.g., a "floppy disk"), and an optical disk drive for reading from or writing to a removable, non-volatile optical disk such as a CD-ROM, DVD-ROM or other optical media can be provided. In such instances, each can be connected to bus 18 by one or more data media interfaces. As will be further depicted and described below, memory 28 may include at least one program product having a set (e.g., at least one) of program modules that are configured to carry out the functions of embodiments of the invention.

Program/utility 40, having a set (at least one) of program modules 42, may be stored in memory 28 by way of example, and not limitation, as well as an operating system, one or more application programs, other program modules, and program data. Each of the operating system, one or more application programs, other program modules, and program data or some combination thereof, may include an implementation of a networking environment. Program modules 42 generally carry out the functions and/or methodologies of embodiments of the invention as described herein.

Computer system/server 12 may also communicate with one or more external devices 14 such as a keyboard, a pointing device, a display 24, etc.; one or more devices that enable a user to interact with computer system/server 12; and/or any devices (e.g., network card, modem, etc.) that enable computer system/server 12 to communicate with one or more other computing devices. Such communication can occur via Input/Output (I/O) interface(s) 22. Still yet, computer system/server 12 can communicate with one or more networks such as a local area network (LAN), a general wide area network (WAN), and/or a public network (e.g., the Internet) via network adapter 20. As depicted, network adapter 20 communicates with the other components of computer system/server 12 via bus 18. It should be understood that although not shown, other hardware and/or software components could be used in conjunction with computer system/server 12. Examples, include, but are not limited to: microcode, device drivers, redundant processing units, external disk drive arrays, RAID systems, tape drives, and data archival storage systems, etc.

Figure 2:
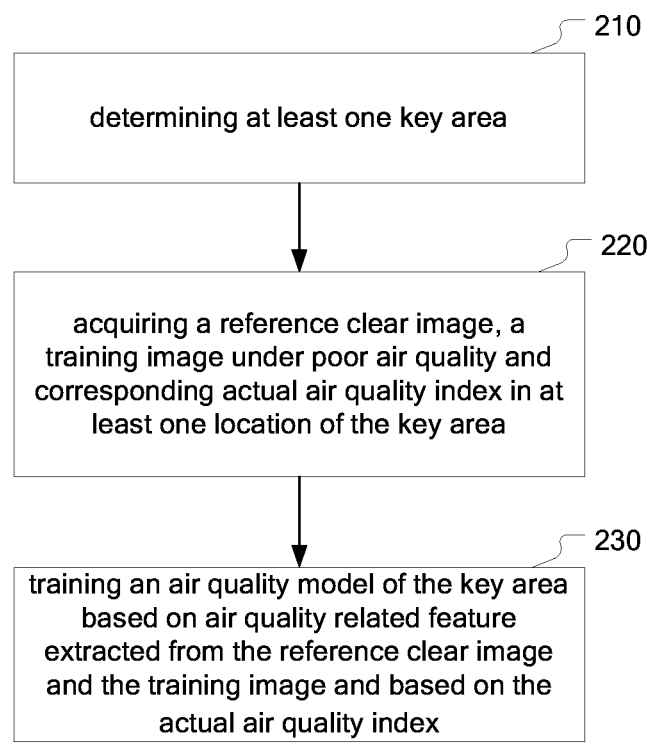
FIG. 2 depicts a flowchart of a method of determining an air quality model according to an embodiment of the invention.

With reference now to FIG. 2, a flowchart of a method of determining an air quality model according to an embodiment of the invention is shown. As shown in FIG. 2, the method at least comprises the following steps.

In step 210, determining at least one key area.

There may be several criteria for selecting a key area, which may be a densely populated area, an area commonly concerned by people, or may be divided by administrative region. Specific selection and setting of a key area will not affect implementation of subsequent steps, thus, those skilled in the art may set a key area according to actual situation.

In step 220, acquiring a reference clear image, a training image under poor air quality and corresponding actual air quality index in at least one location of the key area.

A reference clear image is an image collected when air quality is good. Those skilled in the art can understand that, "clear" and "air quality is good" herein are not an absolute concept, and an ordinary people can easily determine from his/her sense that "air quality is good" at certain time, so as to be able to take a "clear" image. Those skilled in the art can understand that, "poor" air quality herein is relative to air quality under which a reference clear image is acquired, and its main purpose is to acquire a training image that is more blurred than the reference clear image.

In an alternative embodiment, an image at desired location may be randomly selected, which is taken as reference clear image after haze removal process has been applied thereon. There are many available image haze removal methods in the art, such as Dark Channel Prior, contrast-based haze removal method, and these methods are commonly applied in the art and details of which will be omitted here.

In order to acquire abundant training images, training images under different air qualities may be collected at different time, and then for each training image, sensors are used to acquire actual air quality index of the location when that training image is taken. In an alternative embodiment, actual air quality index may also be acquired based on officially published data. There are also many types of air quality indices, such as PM2.5 value, PM10 value and visibility degree etc, which are related to type of a model to be trained.

An image may also be acquired according to different orientations, for example, when a reference clear image is acquired along true north direction, accordingly, training images under different air qualities also need to be acquired along this direction.

In step 230, training an air quality model of the key area based on air quality related feature extracted from the reference clear image and the training image and based on the actual air quality index.

According to an embodiment of the present application, for each location, various air quality related features are extracted from a reference clear image, and various corresponding air quality related features are extracted from a training image, and differences among the features are calculated as training data in training a model. Further, a machine learning algorithm is used to obtain a corresponding function or model between differences of features and air quality indices as the trained model. The machine learning algorithm may use many existing learning algorithms, such as support vector machine (SVM), random forest, AdaBoost etc, and description of which will be omitted here.

The extracted air quality related feature comprises at least one of luminance, chrominance, texture and gradient density. Then, extraction method of part of features will be exemplarily described below.

As to feature of luminance, in an embodiment, it may be embodied as histogram feature of a luminance distribution map, and detailed extraction step may comprise: transforming RGB color value of a pixel into luminance value by using the formula lum=red*0.299+green*0.587+blue*0.114; luminance value of each pixel is within [0,255], calculating accumulative histogram distribution map of the whole image as luminance feature. A 256-dimension histogram may be formed in the finest granularity, or resolution may be reduced, such as a 16-dimension histogram, such that luminance values between 0-7 are classified into a same category.

As to feature of gradient, it may be detected by Prewitt and Sobel operators. In an embodiment, it may be embodied as HOG (Histogram of Oriented Gradient) feature, and detailed extraction step may comprise: transforming the image into a grey scale image; chunking the image such as in 4*4, and calculating gradient histogram distribution map in each chunk, the gradient refers to difference of grey scale colors of two adjacent pixels, which can form a histogram feature vector; combining histogram of each chunk into a large vector as overall gradient HOG feature of the image.

As to feature of texture, in an embodiment, a SIFT feature extraction method may be employed, which comprises: using a SFIT detector to pick up important feature points having rich texture in the image; extracting SIFT features in image regions around each feature point, dimension of this feature is 128-dimension; extracting such features of a large number of images from an image database consisted of a plurality of images and clustering them to form a plurality of cluster centers, so as to obtain a feature dictionary, and an element therein is just a cluster center; for a given image, classifying each feature into a certain cluster after 128-dimension feature of the plurality of feature points has been extracted from that image, and calculating an accumulative histogram of that image with respect to these cluster centers. For example, there are clusters A, B, C, and three feature points are extracted from the image in which two feature points belong to A, another one belongs to B, thus the extracted accumulative histogram feature is (2, 1, 0), which is further normalized to get (⅔, ⅓, 0). For texture detection, a Gabor operator may also be used to scan the image to obtain texture feature. Texture feature may also be determined by using a LBP operator or a grey scale co-occurrence matrix.

The present application mainly utilizes these four types of features, which is a combination having better effect determined by the inventor of the present application after a number of experiments. However, based on teaching of the content disclosed in the application, in the step, those skilled in the art may also select more or less image quality related features and different feature combinations.

Based on type of actual air quality index in the above step, a specific air quality model may be trained in this step, such as a PM2.5 model, a PM10 model, or a visibility degree model.

Figure 3:
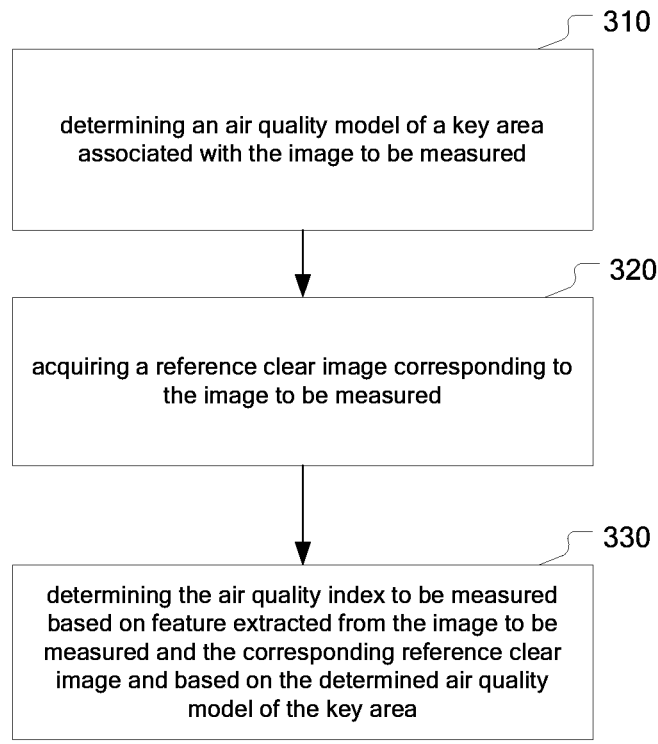
FIG. 3 depicts a flowchart of a method of determining air quality by using the above trained air quality model according to an embodiment of the invention.

With reference now to FIG. 3, a flowchart of a method of determining air quality to be measured by using the above trained air quality model according to an embodiment of the invention is shown. As shown in FIG. 3, the method at least comprises the following steps.

In step 310, determining an air quality model of a key area associated with the image to be measured.

In this step, the image to be measured is at least one real-time image received from a user device. User may take a real-time image at his/her location by using a mobile terminal having a camera device, the image may be one photo, or may be a frame of image in real-time video.

Since the air quality model trained according to the above method is specific to a certain key area, a key area associated with the image to be measured and a corresponding air quality model need to be determined in this step. Specifically, a nearest key area may be selected as associated key area according to location information of the image to be measured.

In step 320, acquiring a reference clear image corresponding to the image to be measured.

In a first embodiment, a first reference clear image is determined based on location of the image to be measured, the first reference clear image is a reference clear image in the associated key area closest to the image to be measured. For example, training image data nearest to the location of the image to be measured taken by user is selected, and then the corresponding reference clear image is directly used as the first reference clear image.

In a second embodiment, a second reference clear image is determined by performing scene matching based on at least one feature of the image to be measured, the second reference clear image is a reference clear image in the associated key area best matched with the image to be measured. The matching may be performed at mobile terminal side or at server side. Specifically, scene matching methods such as bag of words model, HMAX model etc commonly used in the art may be employed.

In a third embodiment, a third reference clear image is determined by performing haze removal on the image to be measured as the corresponding reference clear image. Haze removal algorithms have been introduced above and description of which will be omitted here.

As an improvement, additional information of the image to be measured may also be acquired, the additional information comprises one or more of: shooting parameter information of the image to be measured, geographic location information of the image to be measured. Further, a reference clear image corresponding to the image to be measured is acquired based on the additional information, for example, a reference clear image corresponding to the image to be measured is determined based on sameness or similarity degree of the additional information. Shooting parameter of the image to be measured may comprise pixel information, lens information, shooting angle etc.

In step 330, determining the air quality index to be measured based on feature extracted from the image to be measured and the corresponding reference clear image and based on the determined air quality model of the key area.

If the first reference clear image has been determined according to the location in step 320, a first air quality index is determined based on feature extracted from the image to be measured and the corresponding first reference clear image and based on the determined air quality model of the key area. Further, air quality index of a location to be measured corresponding to the image to be measured is determined at least based on the first air quality index. In an embodiment, the first air quality index may be directly used as air quality index at the location to be measured.

If the second reference clear image has been determined according to scene matching in step 320, a second air quality index is determined based on feature extracted from the image to be measured and the corresponding second reference clear image and based on the determined air quality model of the key area. Further, air quality index of a location to be measured is determined at least based on the second air quality index. In an embodiment, the second air quality index may be directly used as air quality index at the location to be measured. In another embodiment, different weights may be assigned to the first and second air quality indices respectively, and air quality index at the location to be measured is determined by comprehensively considering the two.

If the third reference clear image has been determined according to haze removal processing in step 320, a third air quality index is determined based on feature extracted from the image to be measured and the corresponding third reference clear image and based on the determined air quality model of the key area. Further, air quality index of a location to be measured is determined at least based on the third air quality index. In an embodiment, the third air quality index may be directly used as air quality index at the location to be measured. In another embodiment, different weights may be assigned to the first, second and third air quality indices respectively, and air quality index at the location to be measured is determined by comprehensively considering at least two of them, so as to be able to further improve calculation accuracy.

Figure 4:
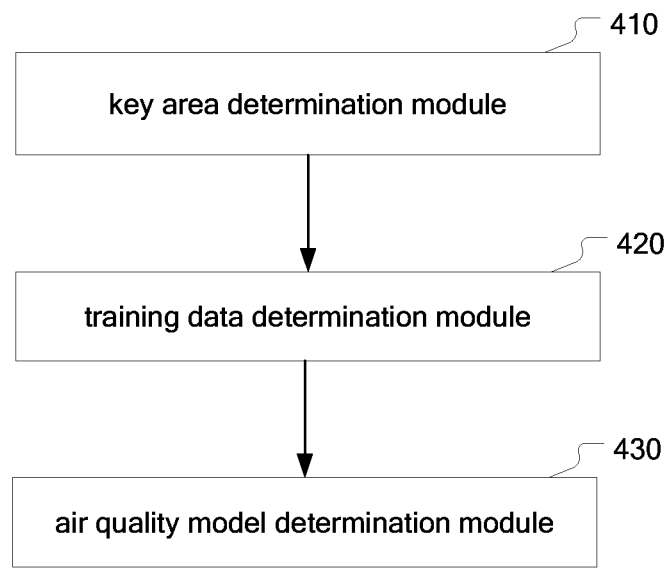
FIG. 4 depicts a block diagram of an apparatus of determining an air quality model according to an embodiment of the invention.

FIG. 4 depicts a block diagram of an apparatus of determining an air quality model according to an embodiment of the invention, the apparatus comprising: a key area determination module 410 configured to determine at least one key area; a training data determination module 420 configured to acquire a reference clear image, a training image under poor air quality and corresponding actual air quality index in at least one location of the key area; an air quality model determination module 430 configured to train an air quality model of the key area based on air quality related feature extracted from the reference clear image and the training image and based on the actual air quality index. Wherein, the feature comprises at least one of: luminance, chrominance, texture and density gradient.

Figure 5:
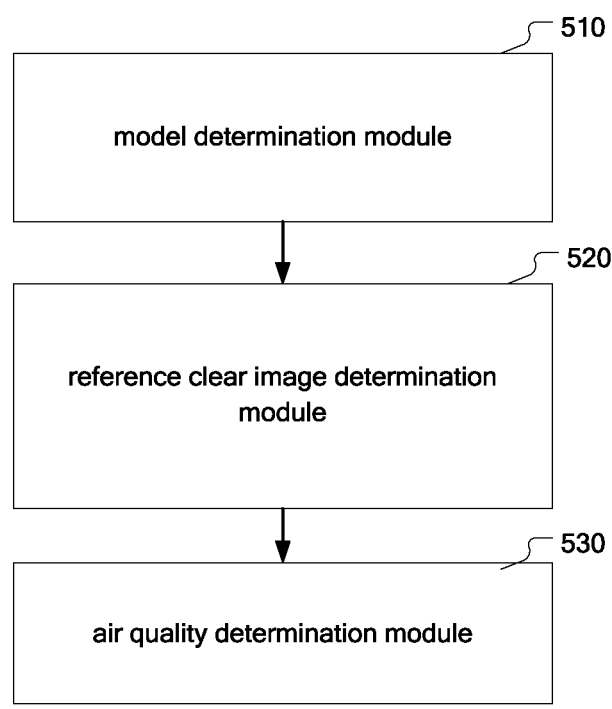
FIG. 5 depicts a block diagram of an apparatus of determining air quality by using the above trained air quality model according to an embodiment of the invention.

FIG. 5 depicts a block diagram of an apparatus of determining air quality to be measured by using the above trained air quality model according to an embodiment of the invention, the apparatus comprising: a model determination module 510 configured to determine an air quality model of a key area associated with the image to be measured; a reference clear image determination module 520 configured to acquire a reference clear image corresponding to the image to be measured; an air quality determination module 530 configured to determine the air quality index to be measured based on air quality related feature extracted from the image to be measured and the corresponding reference clear image and based on the determined air quality model of the key area.

In an embodiment, the reference clear image determination module 520 comprises: a module configured to determine a first reference clear image based on location of the image to be measured, the first reference clear image is a reference clear image in the associated key area closest to the image to be measured; the air quality determination module 530 comprises: a module configured to determine the air quality index to be measured based on the first reference clear image.

In an embodiment, the reference clear image determination module 520 comprises: a module configured to determine a second reference clear image by performing scene matching based on at least one feature of the image to be measured, the second reference clear image is a reference clear image in the associated key area best matched with the image to be measured; the air quality determination module 530 comprises: a module configured to determine the air quality index to be measured based on the second reference clear image.

In another embodiment, the reference clear image determination module 520 comprises: a module configured to acquire a third reference clear image by performing haze removal on the image to be measured; the air quality determination module 530 comprises: a module configured to determine the air quality index to be measured based on the third reference clear image.

In an embodiment, the apparatus shown in FIG. 5 further comprising: a module configured to acquire additional information of the image to be measured, the additional information comprises one or more of: shooting parameter information of the image to be measured, geographic location information of the image to be measured; the reference clear image determination module comprises: a module configured to acquire a reference clear image corresponding to the image to be measured based on the additional information.

With the technology solution of the present application, air quality can be determined based on an image at any time and anywhere, and may bring significant convenience to user. Furthermore, since an air quality model is determined in a manner of machine learning, advantage of big data may be utilized as much as possible, such that the determined air quality model is more accurate and can be better distinguished from conventional solution. When the technology solution of the present application is realized through a general purpose computer system shown in FIG. 1, the computer system shown in FIG. 1 becomes a hardware device of determining an air quality model or a special purpose device of determining air quality index to be measured based on an image to be measured.

The flowchart and block diagrams in the Figures illustrate the architecture, functionality, and operation of possible implementations of systems, methods and computer program products according to various embodiments of the present invention. In this regard, each block in the flowchart or block diagrams may represent a module, segment, or portion of code, which comprises one or more executable instructions for implementing the specified logical function(s). It should also be noted that, in some alternative implementations, the functions noted in the block may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

The invention claimed is:

1. A method of determining an air quality in real-time at a location from a mobile terminal image, the method comprising:
   determining, by one or more computer processors, an image to be measured, wherein the image is received from a user of a mobile terminal with a camera device;
   determining, by one or more computer processors, an air quality model of at least one key area, the at least one key area including a key area associated with the image to be measured;
   acquiring, by one or more computer processors, a reference clear image corresponding to the image to be measured; and
   determining, by one or more computer processors, an air quality index of a location to be measured based on an air quality related feature extracted from the image to be measured, the corresponding reference clear image, and the determined air quality model of the key area associated with the image to be measured.

2. The method according to claim 1, wherein the air quality related feature comprises at least one of: a luminance, a texture and a density gradient.

3. The method according to claim 1, wherein determining an air quality model of at least one key area comprises:
   determining, by one or more computer processors, the at least one key area;
   acquiring, by one or more computer processors, a reference clear image, a training image under poor air quality and corresponding actual air quality index in at least one location of the at least one key area; and
   training, by one or more computer processors, an air quality model of the at least one key area based on an air quality related feature extracted from the reference clear image and the training image and based on the actual air quality index.

4. The method according to claim 1, wherein, acquiring a reference clear image corresponding to the image to be measured comprises: determining a first reference clear image based on the location of the image to be measured, the first reference clear image is a reference clear image in an associated key area closest to the image to be measured; and
   wherein determining the air quality index to be measured based on the air quality feature extracted from the image to be measured, the corresponding reference clear image and the determined air quality model comprises: determining the air quality index of the location to be measured at least based on the first reference clear image.

5. The method according to claim 1, wherein, acquiring a reference clear image corresponding to the image to be measured comprises: determining a second reference clear image by performing scene matching based on at least one feature of the image to be measured, the second reference clear image is a reference clear image in the associated key area best matched with the image to be measured; and
   wherein determining the air quality index of the location to be measured based on the air quality feature extracted from the image to be measured, the corresponding reference clear image and the determined air quality model of the key area comprises: determining the air quality index of the location to be measured at least based on the second reference clear image.

6. The method according to claim 1, wherein, acquiring a reference clear image corresponding to the image to be measured comprises: determining a third reference clear image by performing haze removal on the image to be measured; and wherein determining the air quality index of the location to be measured based on the air quality feature extracted from the image to be measured, the corresponding reference clear image and the determined air quality model of the key area comprises: determining the air quality index of the location to be measured at least based on the third reference clear image.

7. The method according to claim 1, further comprising:

acquiring, by one or more computer processors, additional information of the image to be measured, the additional information comprises at least one of: shooting parameter information of the image to be measured and geographic location information of the image to be measured; and wherein acquiring a reference clear image corresponding to the image to be measured comprises: acquiring, by one or more computer processors, a reference clear image corresponding to the image to be measured based on the additional information.

8. A computer system of determining an air quality in real-time at a location from a mobile terminal image, the computer system comprising:

one or more computer processors;

one or more computer readable storage devices; and program instructions stored on the one or more computer readable storage devices for execution by at least one of the one or more computer processors, the stored program instructions comprising:

program instructions to determine an image to be measured, wherein the image is received from a user of a mobile terminal with a camera device;

program instructions to determine an air quality model of at least one key area, the at least one key area including a key area associated with the image to be measured;

program instructions to a reference clear image corresponding to the image to be measured; and program instructions to determine an air quality index of a location to be measured based on an air quality related feature extracted from the image to be measured, the corresponding reference clear image, and the determined air quality model of the key area associated with the image to be measured.

9. The computer system according to claim 8, wherein the air quality related feature comprises at least one of: a luminance, a texture and a density gradient.

10. The computer system according to claim 8, further comprising, for an image to be measured:

program instructions to determine the at least one key area;

program instructions to a reference clear image, a training image under poor air quality and corresponding actual air quality index in at least one location of the at least one key area; and program instructions to train an air quality model of the at least one key area based on an air quality related feature extracted from the reference clear image and the training image and based on the actual air quality index.

11. The computer system according to claim 8, wherein, program instructions to acquire a reference clear image corresponding to the image to be measured comprise: program instructions to determine a first reference clear image based on the location of the image to be measured, the first reference clear image is a reference clear image in an associated key area closest to the image to be measured; and wherein the program instructions to determine the air quality index of the location to be measured based on the air quality feature extracted from the image to be measured, the corresponding reference clear image and the determined air quality model comprise: program instructions to determine the air quality index of the location to be measured at least based on the first reference clear image.

12. The computer system according to claim 8, wherein, program instructions to acquire a reference clear image corresponding to the image to be measured comprise: program instructions to determine a second reference clear image by performing scene matching based on at least one feature of the image to be measured, the second reference clear image is a reference clear image in the associated key area best matched with the image to be measured; and wherein the program instructions to determine the air quality index of the location to be measured based on the air quality feature extracted from the image to be measured, the corresponding reference clear image and the determined air quality model of the key area comprise: program instructions to determine the air quality index of the location to be measured at least based on the second reference clear image.

13. The computer system according to claim 8, wherein, program instructions to acquire a reference clear image corresponding to the image to be measured comprise: program instructions to determine a third reference clear image by performing haze removal on the image to be measured; and wherein the program instructions to determine the air quality index of the location to be measured based on the air quality feature extracted from the image to be measured, the corresponding reference clear image and the determined air quality model of the key area comprises: program instructions to determine the air quality index of the location to be measured at least based on the third reference clear image.

14. The computer system according to claim 8, further comprising:

program instructions to acquire additional information of the image to be measured, the additional information comprises at least one of: shooting parameter information of the image to be measured and geographic location information of the image to be measured; and wherein the program instructions to acquire a reference clear image corresponding to the image to be measured comprise: program instructions to acquire a reference clear image corresponding to the image to be measured based on the additional information.

15. A non-transitory computer program product for determining an air quality in real-time at a location from a mobile terminal image, the computer program product comprising:

one or more computer readable storage media and program instructions stored on the one or more computer readable storage media, the program instructions comprising:

program instructions to determine an image to be measured, wherein the image is received from a user of a mobile terminal with a camera device;

program instructions to determine an air quality model of at least one key area, the at least one key area including a key area associated with the image to be measured;

program instructions to a reference clear image corresponding to the image to be measured; and program instructions to determine an air quality index of a location to be measured based on an air quality related feature extracted from the image to be measured, the corresponding reference clear image, and the determined air quality model of the key area associated with the image to be measured.

16. The non-transitory computer program product according to claim 15, wherein the program instructions to determine an air quality model of at least one key area comprises:

program instructions to determine the at least one key area;

program instructions to a reference clear image, a training image under poor air quality and corresponding actual air quality index in at least one location of the at least one key area; and program instructions to train an air quality model of the at least one key area based on an air quality related feature extracted from the reference clear image and the training image and based on the actual air quality index.

17. The non-transitory computer program product according to claim 15, wherein, program instructions to acquire a reference clear image corresponding to the image to be measured comprise: program instructions to determine a first reference clear image based on the location of the image to be measured, the first reference clear image is a reference clear image in an associated key area closest to the image to be measured; and wherein the program instructions to determine the air quality index of the location to be measured based on the air quality feature extracted from the image to be measured, the corresponding reference clear image and the determined air quality model comprise: program instructions to determine the air quality index of the location to be measured at least based on the first reference clear image.

18. The non-transitory computer program product according to claim 15, wherein, program instructions to acquire a reference clear image corresponding to the image to be measured comprise: program instructions to determine a second reference clear image by performing scene matching based on at least one feature of the image to be measured, the second reference clear image is a reference clear image in the associated key area best matched with the image to be measured; and wherein the program instructions to determine the air quality index of the location to be measured based on the air quality feature extracted from the image to be measured, the corresponding reference clear image and the determined air quality model of the key area comprise: program instructions to determine the air quality index of the location to be measured at least based on the second reference clear image.

19. The non-transitory computer program product according to claim 15, wherein, program instructions to acquire a reference clear image corresponding to the image to be measured comprise: program instructions to determine a third reference clear image by performing haze removal on the image to be measured; and wherein the program instructions to determine the air quality index of the location to be measured based on the air quality feature extracted from the image to be measured, the corresponding reference clear image and the determined air quality model of the key area comprises: program instructions to determine the air quality index of the location to be measured at least based on the third reference clear image.

20. The non-transitory computer program product according to claim 15, further comprising:

program instructions to acquire additional information of the image to be measured, the additional information comprises at least one of: shooting parameter information of the image to be measured and geographic location information of the image to be measured; and wherein the program instructions to acquire a reference clear image corresponding to the image to be measured comprise: program instructions to acquire a reference clear image corresponding to the image to be measured based on the additional information.

* * * * *